United States Patent [19]

Wang et al.

[11] Patent Number: 5,473,098

[45] Date of Patent: Dec. 5, 1995

[54] PROCESS FOR THE PREPARATION OF STILBENEDICARBOXYLATE ESTERS

[75] Inventors: Richard H. S. Wang, Kingsport; Carl A. Bryan, Jr., Piney Flats; Bill A. Eller, Gray, all of Tenn.

[73] Assignee: Eastman Chemical Company, Kingsport, Tenn.

[21] Appl. No.: 398,840

[22] Filed: Mar. 6, 1995

[51] Int. Cl.$^6$ ................................. C07C 67/343
[52] U.S. Cl. .............................. 560/96; 560/76
[58] Field of Search ........................... 560/96, 76

[56] References Cited

U.S. PATENT DOCUMENTS

| | | |
|---|---|---|
| 3,586,673 | 6/1971 | Bloom et al. |
| 4,713,472 | 12/1987 | Van Sickle .................. 560/53 |
| 4,789,755 | 12/1988 | Van Sickle .................. 560/78 |
| 5,113,010 | 5/1992 | Langer et al. |

OTHER PUBLICATIONS

"A Practical Approach to Homo Trialkyl Phosphonates", Veejendra K. Yadav, Synthetic Communications, 20(2), 239–246 (1990).
"The Syntehsis and Reactions of Organic Compounds", Comprehensive Organic Chemistry, Barton et al., vol. 2, (1979).
J. Amer. Chem. Soc., 83, 1733 (1961).
J. Organic Chemistry, 26, 5243, (1961).

*Primary Examiner*—José G. Dees
*Assistant Examiner*—Samuel Barts
*Attorney, Agent, or Firm*—J. Frederick Thomsen; Harry J. Gwinnell

[57] ABSTRACT

Disclosed is a process for the preparation of 4,4'-stilbenedicarboxylate esters by a 4-step process starting with an alkyl p-formylbenzoate and utilizing intermediate phosphite and phosphonate compounds. The steps comprise (1) preparing an alkyl p-(hydroxymethyl)benzoate by hydrogenating an alkyl p-formylbenzoate;
(2) contacting the alkyl p-(hydroxymethyl)benzoate of step (1) with a trialkyl phosphite to obtain a phosphite ester compound having the formula:

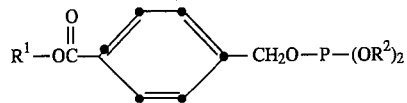

(3) contacting the phosphite ester of step (2) with a catalytic amount of iodine to rearrange the phosphite ester to the corresponding phosphonate ester;
and
(4) contacting the phosphonate ester compound of step (3) with an alkyl p-formylbenzoate in the presence of an alkali metal alkoxide and an inert solvent to obtain the dialkyl 4,4'-stilbenedicarboxylate.

6 Claims, No Drawings

PROCESS FOR THE PREPARATION OF STILBENEDICARBOXYLATE ESTERS

This invention pertains to a novel process for the preparation of 4,4'-stilbenedicarboxylate esters. More specifically, this invention pertains to a 4-step process for the synthesis of dialkyl 4,4'-stilbenedicarboxylates from alkyl p-formylbenzoates utilizing intermediate phospthite and phosphonate compounds.

Dialkyl 4,4'-stilbenedicarboxylates and 4,4'-stilbenedicarboxylic acid are used in the manufacture of optical brighteners or whiteners. For example, U.S. Pat. No. 4,921,964 discloses the preparation of bis(2-benzoxazolyl)stilbene compounds by the reaction of dialkyl stilbenedicarboxylate esters with various 2-aminophenol compounds in the presence of certain solvents and catalysts. Optical brighteners are used extensively in synthetic plastics and fibers to improve the appearance, e.g., the apparent whiteness, thereof. The preparation of a mixture of 4,4'-bibenzyldicarboxylic and 4,4'-stilbenedicarboxylic acids by heating a stoichiometric excess of p-toluic acid with sulfur is disclosed in U.S. Pat. No. 2,677,703. The disadvantages involved in this method for producing 4,4'-stilbene-dicarboxylic acid include (i) high temperatures in the range of 250° to 290° C. are required, (ii) the product mixture containing the starting material, p-toluic acid, and the 2 products, 4,4'-bibenzyldicarboxylic and 4,4'-stilbenedicarboxylic acids, are very difficult to separate, (iii) the low yields, e.g., 40% at best, obtained, and (iv) the necessity to prevent the hydrogen sulfide produced from escaping by costly scrubbing procedures.

It also is known to heat a stoichiometric excess of p-toluic acid with sulfur at 265° C. at a pressure of about 5.5 bars absolute in the presence of nitrogen to obtain 4,4'-stilbenedicarboxylic acid in a 34% yield based on the amount of sulfur used A known method for synthesizing dimethyl 4,4'-stilbenedicarboxylate comprises the steps of (1) contacting methyl p-formylbenzoate with hydrogen sulfide at 0° C. in the presence of hydrochloric acid to produce a cyclic trisulfide compound and (2) heating the cyclic trisulfide compound at 220° to 260° C. in the presence of copper and diphenyl ether. Dimethyl 4,4'-stilbenedicarboxylate is obtained in an overall yield, based on the methyl p-formylbenzoate starting material, of 37.5%. Both of these methods, like the process of U.S. Pat. No. 2,677,703, produce hydrogen sulfide. These processes require the use of special, dedicated equipment and are not well suited for use in general purpose equipment. Additional methods for preparing stilbene compounds are described by K. B. Becker, Synthesis of Stilbenes, Synthesis, May 1983, 341–368 and U.S. Pat. No. 5,113,010.

We have developed a process which does not require the use of sulfur and may be operated at moderate process conditions in general purpose, chemical manufacturing equipment. The process of the present invention provides a novel method for producing a dialkyl 4,4'-stilbenedicarboxylate having the formula

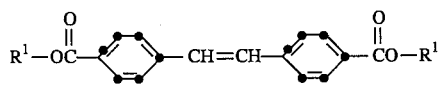  (I)

from an alkyl p-formylbenzoate compound by the steps comprising:

(1) preparing an alkyl P-(hydroxymethyl)benzoate having the formula

  (III)

by hydrogenating an alkyl p-formylbenzoate having the formula

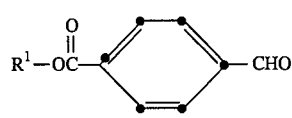  (II)

under hydrogenation conditions of temperature and pressure in the presence of a nickel hydrogenation catalyst;

(2) contacting the alkyl p-(hydroxymethyl)benzoate of step (1) with a trialkyl phosphite having the formula $(R^2O)_3P$ to obtain a phosphite ester compound having the formula:

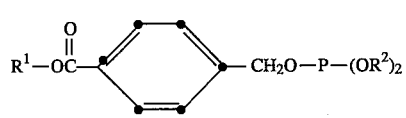  (IV)

(3) contacting the phosphite ester of step (2) with a catalytic amount of iodine to rearrange the phosphite ester to a phosphonate ester having the formula:

  (V)

and (4) contacting the phosphonate ester compound of step (3) with an alkyl p-formylbenzoate, e.g., having formula (II), in the presence of an alkali metal alkoxide and an inert solvent to obtain the dialkyl 4,4'-stilbenedicarboxylate;

wherein $R^1$ is alkyl of 1 to 6 carbon atoms and $R^2$ is alkyl of 2 to 6 carbon atoms. The alkyl p-formylbenzoate, e.g., methyl p-formylbenzoate, used in steps (1) and (4) is produced in large amounts as a byproduct in the manufacture of dimethyl terephthalate which is used in the production of poly(ethylene terephthalate) polymer. The 4-step process may be operated in general purpose equipment in which steps (2), (3) and (4) may be carried out in the same reactor.

The first step of the process is carried out in pressure equipment wherein an alkyl p-formylbenzoate such as methyl p-formylbenzoate is selectively and catalytically hydrogenated at a temperature of about 40 to 110° C. and a pressure of about 20 to 70 bars absolute in the presence of a nickel hydrogenation catalyst and an inert, organic solvent. The catalyst preferably is Raney nickel or a supported nickel catalyst such as nickel on a silica/alumina catalyst support material wherein nickel constitutes about 1–70 weight percent of the catalyst. The hydrogenation usually is performed in the presence of an inert, organic solvent such as, for example, aliphatic and aromatic hydrocarbons, e.g., hexane, heptane, benzene, toluene and the xylenes; chlorinated, aromatic hydrocarbons, e.g., chlorobenzene and dichlorobenzene; and alkyl carboxylate esters, e.g., $C_1$–$C_4$ alkyl esters of carboxylic acids containing 2 to 4 carbon atoms.

The preferred hydrogenation conditions comprise a temperature in the range of about 60° to 75° C. and a pressure of about 40 to 60 bars absolute. Normally, after separation of the catalyst, for example, by filtration, and removal of most or essentially all of the solvent by distillation, the product of step (1) is used in step (2) without further purification.

Step (2) is carried out by simply heating a mixture of the alkyl p-(hydroxymethyl)benzoate from step (1) and a trialkyl phosphite at a temperature of about 120 to 160° C. Step (2) conveniently is performed using an excess of the trialkyl phosphite as the reaction solvent or medium. For example, the mole ratio of trialkyl phosphite to the alkyl p-(hydroxymethyl)benzoate may be in the range of about 10:1 to 1:1, preferably in the range of about 5:1 to 2:1. Upon completion of step (2), the excess (unreacted) trialkyl phosphite may be removed from the product by distillation.

Step (3) is carried out by heating a mixture of the phosphite ester of formula (IV) with a catalytic amount of molecular iodine at a temperature in the range of about 120° to 180° C. The amount of iodine used usually will be an amount which gives an iodine:phosphite ester weight ratio in the range of about 1:50 to 1:300 with a weight ratio in the range of about 1:100 to 1:200 being preferred. Although not necessary, the use of an inert solvent may be preferred to dissipate the heat of reaction. Inert solvents which may be used include dimethylformamide, dimethylacetamide, glycol diethers, glycol diesters, glycol ether esters and haloaromatic compounds. Step (3) preferably is conducted at a temperature of about 140° to 150° C.

The fourth step of the process of the present invention comprises contacting the phosphonate ester compound of step (3) with an alkyl p-formylbenzoate in the presence of an alkali metal alkoxide and an inert solvent to obtain the dialkyl 4,4'-stilbenedicarboxylate. Examples of the alkali metal alkoxides which may be used in step (4) include the sodium, potassium, lithium and cesium alkoxides containing 1 to 4 carbon atoms. The amount of alkali metal alkoxide used typically is at least one mole alkali metal alkoxide per mole of alkyl p-formylbenzoate, preferably about 1.2 to 2.0 moles alkali metal hydroxide per mole of alkyl p-formylbenzoate. Step (4) typically is carried out at a temperature of about 25° to 35° C. in the presence of an inert, organic solvent such as the polar, aprotic solvents described above.

With reference to step (3), the iodine-catalyzed isomerization of trimethyl phosphite to the corresponding dimethyl methylphosphonate is described by V. K. Yadav in Synthetic Communications, 20(2), 239–246 (1990). With reference to step (4), the reaction of diethyl p-carboxybenzylphosphonate with p-(2-benzoxazolyl)benzaldehyde in the presence of DMSO and sodium methoxide to produce 4-(2'-benzoxazolyl)-4'-stilbenecarboxylic acid is described in Example 22 of U.S. Pat. No. 3,586,673. Seus et al., Journal of Organic Chemistry, 26, 5243 (1961) describe the preparation of stilbene and heterocyclic analogs by heating a mixture of diethyl benzylphosphonate, benzaldehyde or a heterocyclic carboxaldehyde, sodium methoxide and dimethylformamide. The novelty and inventive merit of the present process is predicated primarily on the unique combination of steps which require a minimum use of equipment to operate on a commercial scale and on the use of an abundant starting material that is available as a byproduct from commercial dimethyl terephthalate processes.

The process of the present invention is further illustrated by the following examples.

STEP (1)

A mixture of methyl 4-formylbenzoate (500 g, 3.05 mole), Raney nickel (25 g) and toluene (1000 mL) is heated in an autoclave between 60 and 75° C. under a hydrogen atmosphere at between 41 and 44 bars absolute for 3.5 hours. The hydrogen pressure then is released and the catalyst removed from the reaction mixture by filtration at 40° to 60° C. The toluene is removed by distillation and the product, methyl 4-(hydroxymethyl)benzoate obtained in a 90% yield, is used in the next step without further purification.

STEP (2)

A mixture of methyl 4-(hydroxymethyl) benzoate (16.6 g, 0.1 mole) and triethyl phosphite (48 g, 50 mL, 0.29 mole) is heated at 150° C. for 2 hours while low boilers (mainly ethanol) are distilled off a 80° to 85° C. Under reduced pressure (approximately 100 torr) and at a temperature not exceeding 125° C., the excess triethyl phosphite is distilled from the reaction mixture over a 30 minute period of time. The 4-(methoxycarbonyl)benzyl diethyl phosphite product is used without purification in the third step.

STEP (3)

The product (0.1 mole) of step (2) is added slowly over a period of 8 minutes to a hot solution of iodine (0.2 g) in dimethylformamide (DMF, 50 mL) and the mixture is maintained at 140° C. for 3 hours. This solution containing the product, diethyl 4-(methoxycarbonyl)benzylphosphonate, is used in the fourth step.

STEP (4)

DMF (100 mL) and methyl 4-formylbenzoate (13.9 g, 0.13 mole) are added to the product solution from step (3) at a temperature of 25° to 28° C. Sodium methoxide (7 g) is added to the solution while maintaining the temperature at 25° to 35° C. by means of a water bath. The reaction mixture is heated at 25° to 35° C. for an additional 4 hours and then water (100 mL) is slowly added at 25° to 35° C. (with water bath cooling as necessary) to precipitate the product. After stirring for 1 hour, the product, dimethyl 4,4'-stilbenedicarboxylate, is collected by filtration, washed with water until the filtrate has a pH of 5 to 7 and then washed with methanol (2×50 mL). After drying at 60° C. under vacuum, dimethyl 4,4'-stilbenedicarboxylate is obtained in a 65% yield based on the amount of methyl 4-(hydroxymethyl)benzoate employed.

The invention has been described in detail with particular reference to preferred embodiments thereof, but it will be understood that variations and modifications can be effected within the spirit and scope of the invention.

We claim:

1. Process for the preparation of a dialkyl 4,4'-stilbenedicarboxylate having the formula

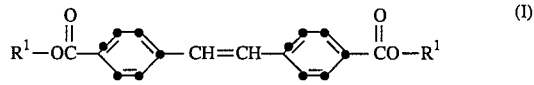

from an alkyl p-formylbenzoate compound by the steps comprising:

(1) preparing an alkyl p-(hydroxymethyl)benzoate having the formula

by hydrogenating an alkyl p-formylbenzoate having the formula

under hydrogenation conditions of temperature and pressure in the presence of a nickel hydrogenation catalyst;

(2) contacting the alkyl p-(hydroxymethyl)benzoate of step (1) with a trialkyl phosphite having the formula $(R^2O)_3P$ to obtain a phosphite ester compound having the formula:

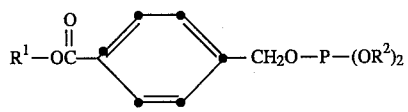

(3) contacting the phosphite ester of step (2) with a catalytic amount of iodine to rearrange the phosphite ester to a phosphonate ester having the formula:

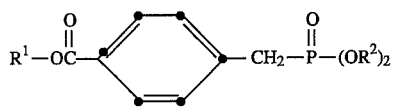

and (4) contacting the phosphonate ester compound of step (3) with an alkyl p-formylbenzoate in the presence of an alkali metal alkoxide and an inert solvent to obtain the dialkyl 4,4'-stilbenedicarboxylate;

wherein $R^1$ is alkyl of 1 to 6 carbon atoms and $R^2$ is alkyl of 2 to 6 carbon atoms.

2. Process according to claim 1 wherein step (1) comprises hydrogenating the alkyl p-formylbenzoate at a temperature of about 40° to 100° C. and a pressure of about 20 to 70 bars absolute in the presence of Raney nickel or a supported nickel catalyst and an inert, organic solvent.

3. Process according to claim 2 wherein step (2) comprises heating a mixture of the alkyl p-(hydroxymethyl)benzoate and an excess of the trialkyl phosphite at a temperature of about 120° to 160° C. and step (3) comprises heating the phosphite ester at 120° to 180° C. in the presence of a catalytic amount of iodine and an inert solvent.

4. Process according to claim 3 wherein step (4) comprises contacting the phosphonate ester compound of step (3) with an alkyl p-formylbenzoate in the presence of an alkali metal alkoxide and an inert solvent at a temperature of about 25° to 35° C.

5. Process for the preparation of dimethyl 4,4'-stilbenedicarboxylate from methyl p-formylbenzoate by the steps comprising:

(1) preparing methyl p-(hydroxymethyl)benzoate by hydrogenating methyl p-formylbenzoate at a temperature of about 60° to 75° C. and a pressure of about 40 to 60 bars absolute in the presence of a nickel hydrogenation catalyst selected from Raney nickel and supported nickel catalysts and an inert solvent;

(2) contacting the methyl p-(hydroxymethyl)benzoate of step (1) with triethyl phosphite to obtain diethyl p-(methoxycarbonyl)benzyl phosphite;

(3) contacting the phosphite ester of step (2) with a catalytic amount of iodine at a temperature of about 120° to 180° C. in the presence of an inert solvent to rearrange the phosphite ester to diethyl p-(methoxycarbonyl)benzylphosphonate;

and (4) contacting the phosphonate compound of step (3) with methyl p-formylbenzoate at a temperature of about 25° to 35° C. in the presence of an alkali metal alkoxide and an inert solvent to obtain dimethyl 4,4'-stilbenedicarboxylate.

6. Process according to claim 5 wherein step (1) is carried out in the presence of Raney nickel and an inert solvent selected from hexane, heptane, benzene, toluene, the xylenes, chlorobenzene, dichlorobenzene and $C_1$–$C_4$ alkyl esters of carboxylic acids containing 2 to 4 carbon atoms; step (2) is carried out using about 2 to 5 moles of triethyl phosphite per mole of methyl p-(hydroxymethyl)benzoate; and step (3) is carried out at about 140° to 150° C. in the presence of a catalytic amount of iodine and dimethylformamide.

* * * * *